(12) United States Patent
Wood et al.

(10) Patent No.: US 7,799,162 B2
(45) Date of Patent: Sep. 21, 2010

(54) COMPOSITE WEBS WITH ELASTIC COMPOSITE STRUCTURES

(75) Inventors: Leigh E. Wood, Woodbury, MN (US); Randall L. Alberg, Maplewood, MN (US); Byron M. Jackson, Forest Lake, MN (US); Dennis L. Becker, Vadnais Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 358 days.

(21) Appl. No.: 10/842,323

(22) Filed: May 10, 2004

(65) Prior Publication Data

US 2005/0249915 A1 Nov. 10, 2005

(51) Int. Cl.
*B32B 15/00* (2006.01)

(52) U.S. Cl. ...................................... 156/230
(58) Field of Classification Search ........................ None
See application file for complete search history.

(56) References Cited

U.S. PATENT DOCUMENTS

| | | | |
|---|---|---|---|
| 3,276,944 A | 10/1966 | Levy | |
| 3,304,861 A * | 2/1967 | Magid | 101/152 |
| 3,338,992 A | 8/1967 | Kinney | |
| 3,341,394 A | 9/1967 | Kinney | |
| 3,502,538 A | 3/1970 | Peterson | |
| 3,502,763 A | 3/1970 | Hartman | |
| 3,542,615 A | 11/1970 | Dobo et al. | |
| 3,554,853 A | 1/1971 | Mercer et al. | |
| 3,692,618 A | 9/1972 | Dorschner et al. | |
| 3,899,803 A | 8/1975 | Brumlik | |
| 4,059,713 A | 11/1977 | Mercer | |
| 4,075,379 A | 2/1978 | Lloyd | |
| 4,141,313 A * | 2/1979 | Hefele | 118/212 |
| 4,183,121 A | 1/1980 | Cousins | |
| 4,302,495 A | 11/1981 | Marra | |
| 4,329,309 A | 5/1982 | Kelly | |
| 4,340,563 A | 7/1982 | Appel et al. | |
| 4,440,709 A | 4/1984 | Rasmussen | |
| 4,636,419 A | 1/1987 | Madsen et al. | |
| 4,661,389 A | 4/1987 | Mudge et al. | |
| 4,753,838 A | 6/1988 | Kimura et al. | |
| 4,887,339 A | 12/1989 | Bellanger | |

(Continued)

FOREIGN PATENT DOCUMENTS

EP 0 096 458 A1 12/1983

(Continued)

OTHER PUBLICATIONS

"ASTM D 1238-01, Standard Test Method for Melt Flow Rates of Thermoplastics by Extrusion Plastomer," Annual Book of ASTM Standards, vol. 08.01, pp. 266-278.

*Primary Examiner*—Philip C Tucker
*Assistant Examiner*—Kimberly K McClelland

(57) ABSTRACT

Composite webs having one or more elastic composite structures located on a substrate, methods of manufacturing the composite webs, and articles including the elastic composite structures and substrates are disclosed. The elastic composite structures may preferably include one or more elastic components attached to anchors at two or more locations, wherein the anchors are themselves attached to the substrate. The anchors may preferably be constructed of inelastic polymeric material (and/or exhibit limited to no elasticity in use) and the elastic components may preferably be constructed of elastomeric polymeric material.

61 Claims, 5 Drawing Sheets

U.S. PATENT DOCUMENTS

| | | | |
|---|---|---|---|
| 4,965,122 A | 10/1990 | Morman | |
| 4,981,747 A | 1/1991 | Morman | |
| 5,114,781 A | 5/1992 | Morman | |
| 5,116,662 A | 5/1992 | Morman | |
| 5,226,992 A | 7/1993 | Morman | |
| 5,399,219 A | 3/1995 | Roessler et al. | |
| 5,462,708 A | 10/1995 | Swenson et al. | |
| 5,501,679 A | 3/1996 | Krueger et al. | |
| 5,667,869 A | 9/1997 | Beretta | |
| 5,685,873 A | 11/1997 | Bruemmer et al. | |
| 5,753,337 A | 5/1998 | Slocumb | |
| 5,885,686 A | 3/1999 | Cederblad et al. | |
| 5,953,797 A | 9/1999 | Provost et al. | |
| 5,983,467 A | 11/1999 | Duffy | |
| 6,054,091 A | 4/2000 | Miller et al. | |
| 6,255,236 B1 | 7/2001 | Cree et al. | |
| 6,391,420 B1 | 5/2002 | Cederblad et al. | |
| 6,406,466 B1 | 6/2002 | Pozniak et al. | |
| 7,195,729 B2 * | 3/2007 | Jackson et al. | 264/214 |
| 7,238,314 B2 * | 7/2007 | Jackson et al. | 264/214 |
| 7,390,451 B2 * | 6/2008 | Jackson et al. | 264/214 |
| 2001/0016245 A1 | 8/2001 | Tuman et al. | |
| 2001/0018110 A1 | 8/2001 | Tuman et al. | |
| 2003/0084996 A1 | 5/2003 | Alberg et al. | |
| 2003/0085485 A1 | 5/2003 | Seidel et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |
| 2003/0091807 A1 | 5/2003 | Desai et al. | |
| 2004/0178544 A1 | 9/2004 | Jackson et al. | |
| 2007/0141300 A1 * | 6/2007 | Jackson et al. | 428/99 |
| 2007/0176325 A1 * | 8/2007 | Jackson et al. | 264/288.4 |

FOREIGN PATENT DOCUMENTS

| | | |
|---|---|---|
| EP | 0 096 458 B1 | 12/1986 |
| EP | 0 580 073 B1 | 1/1998 |
| EP | 0 860 930 | 3/1998 |
| EP | 0 892 320 | 1/1999 |
| JP | HEI 10-53963 A | 2/1998 |
| WO | WO 96/10481 A1 | 4/1996 |
| WO | WO 98/55292 A1 | 12/1998 |
| WO | WO 99/10166 A1 | 3/1999 |
| WO | WO 00/19952 A1 | 4/2000 |
| WO | WO 00/20206 | 4/2000 |
| WO | WO 00/37003 A2 | 6/2000 |
| WO | WO 00/37003 A3 | 6/2000 |
| WO | WO 00/50229 A1 | 8/2000 |
| WO | WO 02/00412 | 1/2002 |
| WO | WO 03/039853 A1 | 5/2003 |

* cited by examiner

COMPOSITE WEBS WITH ELASTIC COMPOSITE STRUCTURES

The present invention relates to the field of composite webs with elastic structures and methods of manufacturing the same.

The manufacture of composite webs that exhibit elasticity, i.e., the ability to at least partially recover their original shape after moderate elongation, may be desired for a number of reasons. For example, elasticity may be useful in connection with fastening systems for items such as garments (e.g., diapers, training pants, gowns, bedding, etc.). Elasticity in garments can provide what may be referred to as dynamic fit, i.e., the ability to stretch and recover in response to movement by the wearer.

Elasticity may also be useful in connection with other articles or devices. For example, some fasteners may provide more consistent attachment if the fastener is held in tension that can be supplied by stretching the fastener and relying on the recovery forces to provide the desired tension. In other instances, elasticity may allow for easy adjustment of the size or length of a fastener or other article.

Although elasticity may be beneficial in a variety of different applications, it may raise issues in manufacturing. Many attempts to provide elasticity to, e.g., composite webs and other articles, rely on separate elastic components that are, e.g., glued or sewn to a substrate or other nonelastic member to provide the desired elasticity. The manufacture of such composite articles may be problematic in that secure attachment of the elastic components may be difficult to achieve and/or maintain. When attaching elastic components using adhesive (e.g., pressure sensitive adhesive), a common problem is adhesive creep, i.e., the tendency of the elastic component to move across the surface of the web or other article in response to shear forces.

Further, the cost and difficulty of providing and attaching separate elastic components may be relatively high. The handling and attachment of separate elastic components can reduce throughput, cause additional waste (where the separate components are not securely attached), etc.

In other instances, an entire composite web or substrate may exhibit elasticity. For example, many elastic fastening systems rely on the use of elastic laminate backings in which the elastic materials are provided in the form of a film that is coextensive with a substrate. Such an approach may add costs associated with providing a coextensive elastic layer or layers. Further, many elastic materials are not breathable. If the elastic laminate backings are to be used in garments, it may be desirable to perforate the backing to improve its breathability. Such additional processing does, however, add to the cost of producing the elastic laminate backing. Another potential disadvantage of elastic laminate backings is that it may be difficult to provide any adjustment of the elastic recovery forces generated in different portions of the backing.

While a variety of approaches to providing discrete polymeric structures on substrates are disclosed in, e.g., U.S. Patent Application Publication No. U.S. 2003/0085485 A1, filed 5 Nov. 2001 and titled SYSTEMS AND METHODS FOR COMPOSITE WEBS WITH STRUCTURED DISCRETE POLYMERIC REGIONS; U.S. Patent Application Publication No. U.S. 2003/0087098 A1, filed 5 Nov. 2001 and titled COMPOSITE WEBS WITH REINFORCING POLYMERIC REGIONS AND ELASTIC POLYMERIC REGIONS; U.S. Patent Application Publication No. U.S. 2003/0084996 A1, filed 5 Nov. 2001 and titled METHODS FOR PRODUCING COMPOSITE WEBS WITH REINFORCING DISCRETE POLYMERIC REGIONS; U.S. Patent Application Publication No. U.S. 2003/0087059 A1, filed 5 Nov. 2001 and titled COMPOSITE WEBS WITH DISCRETE ELASTIC POLYMERIC REGIONS; U.S. patent application Ser. No. 10/387,699, filed Mar. 13, 2003, and titled POLYMER TRANSFER APPARATUS, METHODS, AND COMPOSITE WEBS; and U.S. patent application Ser. No. 10/744,141, filed Dec. 22, 2003, and titled COMPOSITE WEBS AND CLOSURE SYSTEMS; these approaches may be limited in certain aspects, such as in roll temperatures, the composition of substrates, etc. and those limitations may or may not apply in connection with the present invention.

SUMMARY OF THE INVENTION

The present invention provides composite webs having one or more elastic composite structures located on a substrate, methods of manufacturing the composite webs, and articles including the elastic composite structures and substrates. The elastic composite structures may preferably include one or more elastic components attached to anchors at two or more locations, wherein the anchors are themselves attached to the substrate. The anchors may preferably be constructed of inelastic polymeric material (and/or exhibit limited to no elasticity in use) and the elastic components may preferably be constructed of elastomeric polymeric material.

Composite webs having one or more elastic composite structures attached to a substrate in accordance with the present invention may advantageously provide elasticity to the substrate if the substrate itself is extensible. The substrate itself may, in some instances be elastic, in which case the elastic composite structures may modify the elasticity of the substrate.

The elastomeric and/or inelastic polymeric materials may preferably be thermoplastic materials. As used in connection with the present invention, "thermoplastic" (and variations thereof) means a polymer or polymeric composition that softens when exposed to heat and returns to its original condition or near its original condition when cooled to room temperature. The thermoplastic materials used in connection with the methods of the present invention may preferably be capable of flowing or entering into depressions in a forming tool as described herein.

Suitable polymeric materials for use in connection with the present invention are preferably melt processable, e.g., thermoplastic polymeric materials. Melt processable polymeric materials (also referred to herein as molten polymeric materials) may be described as those polymeric materials that will flow sufficiently to at least partially fill depressions in an otherwise smooth surface, yet not significantly degrade during a melt process. A wide variety of polymeric materials may have suitable melt and flow characteristics for use in connection with the present invention depending on the geometry of the depressions and the processing conditions. It may further be preferred that the melt processable polymeric materials and conditions of processing are selected such that any viscoelastic recovery properties of the polymeric materials do not cause them to significantly withdraw from the depressions during, e.g., wiping of the molten polymeric material as described herein.

In at least some methods according to the present invention in which a forming tool is used to form and transfer the one or more elastic composite structures to the substrate, it may be preferred that the surface of the forming tool be maintained at a roll temperature that is below the melt processing temperature of the polymeric materials being transferred by that forming tool. The melt processing temperature of the polymeric materials used in connection with the present invention is the lowest temperature at which the polymeric material is capable of flowing or entering into depressions in the forming tool (as described herein) under low to moderate pressures (e.g., pressures that may be developed using, e.g., a doctor blade, nip roll, etc.) within a period of, e.g., five seconds or less.

In some instances, the melt processing temperature may be at or slightly above the glass transition temperature for an amorphous polymeric material or at or slightly above the melting temperature for a crystalline or semicrystalline polymeric material. If the polymeric material includes one or more amorphous polymers blended with either or both of one or more crystalline and one or more semicrystalline polymers, then the melt processing temperature is the higher of the highest glass transition temperature of the amorphous polymers or the highest melting temperature of the crystalline and semicrystalline polymers. In addition, it may be preferred that the roll temperature be at least 20° Celsius or more below the temperature of the molten polymeric material as deposited on the forming tool.

One potential advantage of maintaining a relatively cool forming tool is that the molten polymeric material applied to the forming tool (either on its outer surface or within depressions formed therein) may fall below the melt processing temperature of the polymeric material such that it may at least partially freeze or solidify, while at least a portion of the molten polymeric material located distal from the exterior tool surface remains molten long enough to effect transfer of the polymeric material to form the selected components of the elastic composite structures. The preferred result is that the molten polymeric material distal from the exterior tool surface is capable of attaching to the desired component (e.g., the substrate, an anchor, an elastic component, etc.), while the polymeric material in contact with the exterior tool surface releases from that surface cleanly (e.g., is frozen or solidified).

Another potential advantage of maintaining a relatively cool forming tool is that the composition of the substrates to which the molten thermoplastic composition is transferred may not be limited by the forming tool temperature. For example, the tool temperature may be low enough to limit any significant damage to the substrate during the transfer process. As such, the elastic composite structures may be formed on porous and non-porous substrates (such as films) constructed of the same or similar polymeric materials as the elastic composite structures. In some instances involving substrates formed of thermoplastic polymers, the substrate thermoplastic polymer composition may preferably have a melt processing temperature that is at or below the melt processing temperature of the polymeric material used in the elastic composite structures formed thereon. The melt processing temperature of the substrate thermoplastic polymer composition is subject to the same definition of melt processing temperature provided above in connection with the polymeric materials used to form the elastic composite structures. In addition, it may be preferred that the roll temperature be at least 20° Celsius or more below the melt processing temperature of a substrate thermoplastic polymer composition.

Concerns regarding the internal cohesive strength of the substrate and/or the tensile strength of the substrate may be of more concern if the substrate includes a fibrous construction (e.g., woven, nonwoven, or knit fibers) that could be separated from the remainder of the substrate by the forces exerted when, e.g., the substrate is pulled away from the forming tool. These considerations may be limited by the present invention because of the preferred freezing or solidification of the polymeric material in the depressions. Freezing or solidification of the polymeric material can limit any forces exerted on the substrate when the substrate and any attached structures formed thereon by the polymeric material are removed from the forming tool.

Another potential advantage of the methods of the present invention is the ability to transfer one or more masses of polymeric material onto a major surface of a substrate while at least a portion of the polymeric material facing the substrate is molten (i.e., is above its melt processing temperature). If the substrate is, e.g., porous, fibrous, etc., pressure applied to the substrate and the masses of polymeric material during the transfer may enhance attachment of the one or more masses of polymeric material to the substrate by forcing a portion of the molten polymeric material to infiltrate the substrate and/or encapsulate fibers of the substrate. If the substrate is not porous, but is made with a thermoplastic composition that has a melt processing temperature sufficiently low relative to the temperature of the molten polymeric material in the depressions, then attachment of the masses of polymeric material to the substrate may be achieved by intermixing of the polymeric material and the thermoplastic compositions of the substrate.

In one aspect, the present invention provides a method of manufacturing a composite web by delivering molten elastomeric polymeric composition onto a forming tool; maintaining the forming tool at a roll temperature that is below a melt processing temperature of the elastomeric polymeric composition; depositing molten anchor polymeric composition on at least a portion of the elastomeric polymeric composition; transferring the anchor polymeric composition to a first major surface of a base substrate, wherein the transferring includes contacting the first major surface of the substrate with the anchor polymeric composition; and separating the elastomeric polymeric composition from the forming tool after the transferring; wherein a composite web is formed with one or more elastic composite structures on the first major surface of the base substrate, wherein each of the elastic composite structures includes an elastic component attached to two anchors, wherein the anchors include the anchor polymeric composition and wherein the elastic component includes the elastic polymeric composition.

In another aspect, the present invention provides a method of manufacturing a composite web by providing a forming tool having an exterior surface that includes one or more depressions formed therein; delivering a molten elastomeric polymeric composition onto an exterior surface of a forming tool; maintaining the exterior surface of the forming tool at a roll temperature that is below a melt processing temperature of the elastomeric polymeric composition; wiping the molten elastomeric polymeric composition on the exterior surface of the forming tool, wherein at least some of the molten elastomeric polymeric composition enters one or more depressions in the exterior surface of the forming tool; depositing molten anchor polymeric material on at least a portion of the elastomeric polymeric composition, wherein at least a portion of the molten anchor polymeric composition is located on an anchor portion of the elastomeric polymeric composition in the one or more depressions; transferring the anchor polymeric composition to a first major surface of a base substrate, wherein the transferring includes contacting the first major surface of the substrate with the anchor polymeric composition, wherein the first major surface of the base substrate is a porous surface, and wherein a portion of the anchor polymeric composition infiltrates the porous surface after the transferring; and separating the elastic polymeric composition in the one or more depressions and the anchor polymeric composition from the forming tool after the transferring; wherein a composite web is formed that includes one or more elastic composite structures on the first major surface of the base substrate, wherein each of the elastic composite structures includes an elastic component attached to two anchors, wherein the anchors include the anchor polymeric composition and wherein the elastic component include the elastomeric polymeric composition.

In another aspect, the present invention provides a method of manufacturing a composite web by delivering a base substrate and an elastic substrate to a nip; delivering molten anchor polymeric composition between the base substrate and the elastic substrate; wherein a composite web is formed that includes one or more elastic composite structures on the first major surface of the base substrate, wherein each of the elastic composite structures includes an elastomeric component attached to two anchors, wherein the anchors include the anchor polymeric composition and wherein the elastic component includes the elastic substrate.

In another aspect, the present invention provides an elastic composite structure that includes a base substrate with a first major surface; two anchors attached to the first major surface of the base substrate, wherein each anchor of the two anchors includes a mass of an anchor polymeric composition attached to the first major surface of the base substrate; and an elastic component attached to and extending between the two anchors, the elastic component including an elastomeric polymeric composition, wherein the elastic component is not attached to the first major surface of the substrate between the two anchors, and wherein elongation of the base substrate between the two anchors stretches the elastic component.

In another aspect, the present invention provides an elastic composite structure including a base substrate having a porous first major surface; one or more anchors attached to the first major surface of the base substrate, wherein each anchor of the one or more anchors includes a mass of an anchor polymeric composition attached to the first major surface of the base substrate, wherein the porous first major surface is infiltrated by at least a portion of the anchor polymeric composition of each of the anchors; and an elastic component attached to at least one anchor of the one or more anchors, the elastic component including an elastomeric polymeric composition.

In another aspect, the present invention provides an elastic composite structure with a base substrate having a first major surface; two anchors attached to the first major surface of the base substrate, wherein each anchor of the two anchors includes a mass of an anchor polymeric composition adhesively attached to the first major surface of the base substrate; and an elastic component attached to and extending between the two anchors, the elastic component including an elastomeric polymeric composition; wherein, when the elastic composite structure is elongated in a stretch direction extending through the two anchors such that when the elastic component exhibits 50% elongation as measured along the direction, each anchor of the two anchors exhibits 10% or less elongation as measured along the stretch direction.

In another aspect, the present invention provides a garment or an incontinence device including one or more elastic composite structures as described herein.

These and other features and advantages of the present invention may be described below in connection with various illustrative exemplary embodiments of the invention.

BRIEF DESCRIPTIONS OF THE FIGURES

DETAILED DESCRIPTION OF EXEMPLARY EMBODIMENTS

As discussed above, the present invention provides composite webs that include one or more elastic composite structures located on the surface of a substrate, methods of manufacturing the composite webs, and closure articles including the elastic composite structures and substrates and that provide closure elements and systems of the present invention. In the following descriptions of exemplary embodiments of the invention, reference may be made to the accompanying figures which form a part hereof, and in which are shown, by way of illustration, specific exemplary embodiments in which the invention may be practiced. It is to be understood that other embodiments may be utilized and structural changes may be made without departing from the scope of the present invention.

Figure 1:
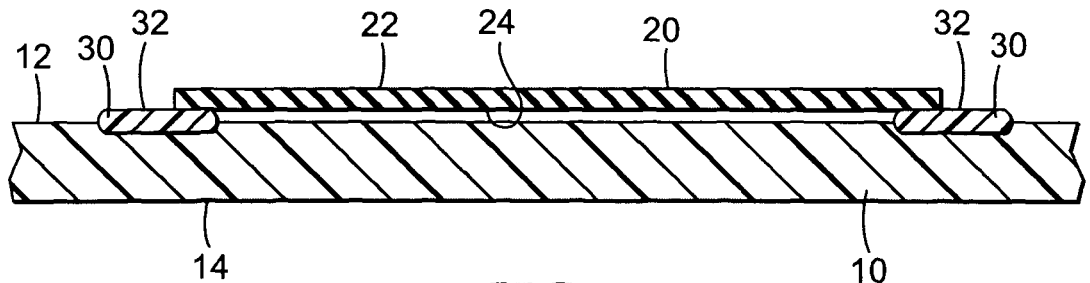
FIG. 1 is a cross-sectional view of a portion of one exemplary composite web according to the present invention.

FIG. 1 is a cross-sectional view of a portion of one composite web in accordance with the present invention. The composite web includes a substrate 10 with a first major surface 12 and a second major surface 14. An elastic composite structure is depicted as located on the first major surface 12 of the substrate 10. The elastic composite structure includes an elastic component 20 attached to anchors 30. The anchors 30 may preferably be spaced apart from each other over the surface 12 of the substrate 10.

It may be preferred that the elastic component 20 be unattached to the surface 12 of the substrate 10 between the anchors 30. In some instances, however, the elastic component 20 may be attached to the surface 12 of the substrate 10 between the anchors 30. In such a situation, however, the attachment of the elastic component 20 to the surface 12 of the substrate 10 may be secondary to the primary attachment between the elastic component 20 and the anchors 30. For example, the attachment between the elastic component 20 and the surface 12 of the substrate 10 may be destroyed by stretching the elastic component 20 and/or the substrate 10.

In some embodiments, the elastic composite structures of the present invention may be provided in a one-sided form in which only one anchor 30 is attached to a base substrate 10 and an elastic component 20 is attached to the anchor 30 (and preferably not otherwise attached to the substrate 10).

The elastic component 20 of the elastic composite structure exhibits elasticity after manufacturing of the elastic composite structure. As such, it may be preferred that the elastic component 20 be constructed of elastomeric polymeric materials as described herein. In some instances, it may be preferred that elastic component 20 be formed in one or more depressions in the surface of a forming tool and transferred to the elastic composite structure as described herein.

As used in connection with the present invention, an "elastic component" means a component that will substantially resume its original shape after being stretched. Further, the elastic component may preferably sustain only small permanent set following deformation and relaxation which set is preferably no greater than about 30 percent and more preferably no greater than about 20 percent of the original length at moderate elongation, e.g., about 50%.

The elastic composite structure also includes anchors 30 attached to the first surface 12 of the substrate 10. The anchors 30 may preferably be constructed of inelastic polymeric material. It may be preferred that the anchors 30 be discrete masses of inelastic polymeric material. By discrete masses, we mean that the different anchors are separated from each other across the surface 12 of the substrate 10. In some instances, however, the anchors 30 may be connected to each other if the extensibility of the substrate 10 between the anchors 30 is not prevented.

Although it may be preferred that the anchors 30 be formed of inelastic polymeric compositions, in some instances the anchors 30 may include elastomeric polymeric materials if the resulting anchors 30 themselves exhibit little or no elasticity relative to the elasticity exhibited by the elastic component 20. For example, it may be preferred that the anchors exhibit elastic recovery of 50% or less after elongation along any in-plane direction over a major surface of the base substrate 10. Alternatively, it may be preferred that the anchors 30 exhibit elastic recovery of 30% or less after elongation, or even elastic recovery of 10% or less after elongation along any in-plane direction over a major surface of the substrate 10.

Another manner of characterizing the anchors in elastic composite structures of the present invention may involve describing the elasticity of the anchors relative to the elastic components. For example, in some embodiments, the anchors may be constructed of elastomeric polymeric materials. The elasticity of the anchors may, however, preferably be less than the elasticity of the elastic components in a given elastic composite structure such that under forces normally experienced by the elastic composite structure, the anchors do not undergo significant elongation when the elastic components are elongating due to the applied forces. The differences in elongation of the anchors and the elastic components may be the result of, e.g., different elastomeric polymeric materials in the anchors and the elastic components, the cross-sectional area of the elastomeric polymeric material in the anchors and the elastic components (e.g., the anchors may be thicker than the elastic components), etc. It may be preferred, for example, that when the elastic composite structure is elongated in a stretch direction extending through two anchors such that the elastic component exhibits 50% elongation as measured along the direction, each anchor of the two anchors exhibits 10% or less elongation as measured along the stretch direction. Alternatively, it may be preferred that when the elastic composite structure is elongated in a stretch direction extending through two anchors such that the elastic component exhibits 25% elongation as measured along the stretch direction, each anchor of the two anchors exhibits 2% or less elongation as measured along the stretch direction. In still another alternative description of relative elasticity, it may be preferred that when the elastic composite structure is elongated in a stretch direction extending through two anchors up to the elastic limit of the elastic component, the anchors exhibit only 20% or less of the elongation of the elastic component, more preferably only 10% or less of the elongation of the elastic component, and even more preferably only 5% or less of the elongation of the elastic component.

Methods of transferring or attaching the anchors 30 to the substrate 10 may take a variety of forms. For example, the anchors 30 may be applied using forming tools with depressions formed in an outer surface thereof, using a smooth tool and a notched doctor blade, or combinations of tools with depressions and notched doctor blades. Examples of some potentially suitable systems, apparatus and methods of attaching anchors 30 to the substrate 10 may be described in, e.g., U.S. Patent Application Publication No. U.S. 2003/0087059 A1, filed 5 Nov. 2001 and titled COMPOSITE WEBS WITH DISCRETE ELASTIC POLYMERIC REGIONS, U.S. patent application Ser. No. 10/387,699, filed Mar. 13, 2003, and titled POLYMER TRANSFER APPARATUS, METHODS, AND COMPOSITE WEBS; and U.S. patent application Ser. No. 10/744,141, filed Dec. 22, 2003, and titled COMPOSITE WEBS AND CLOSURE SYSTEMS.

Other methods of attaching anchors to the substrates of the present invention may also be envisioned. For example, anchors may be attached to substrates using adhesives as discussed herein (see, e.g., FIG. 4 and the corresponding discussion). Other alternative attachment techniques may include, e.g., thermal attachment (e.g., heat sealing, spot welding, extrusion bonding, etc.), ultrasonic attachment, chemical welding (using, e.g., solvents, etc.). In addition, although it may be preferred that the entire surface of each anchor that faces the substrate be attached to the substrate, in some embodiments, only a portion or portions of the surface of the anchor may be attached to the substrate.

The elastic component 20 includes a surface 22 facing away from substrate 10 and a surface 24 facing the substrate 10. Similarly, the anchors 30 include a surface 32 facing away from the substrate 10. The elastic component 20 is attached to the surfaces 32 of the anchors 30.

It may be preferred that the elastic polymeric material of the elastic component 20 attach or bond to the anchors by, e.g., intermixing of the polymeric materials used for the elastic component 20 and the anchors 30 (e.g., surface mixing as seen in, e.g., fusion bonding or heat sealing of, e.g., polymeric materials). In an alternative characterization, it may be preferred that the elastic component be attached directly to the anchors 30 without the aid of, e.g., adhesives or other bonding agents that are applied separately from the polymeric material used to form the anchors 30 themselves. For example, to attach the elastic component 20 to the anchors, it may be preferred that the elastomeric polymeric material of the elastic component 20 be at a temperature above its melt processing temperature while it is in contact with the polymeric material of the anchors 30. It may not be required, or even preferred, that all of the elastomeric polymeric material of the elastic component 20 is above its melt processing temperature. In some instances, it may be sufficient that only the portion of the elastomeric polymeric material facing the anchors 30 be at the melt processing temperature to attach the elastic component 20 to the anchors 30.

Other methods of attaching elastic components to anchors in the elastic composite structures of the present invention may also be envisioned. For example, alternative attachment techniques may include, e.g., thermal attachment (e.g., heat sealing, spot welding, etc.), ultrasonic attachment, chemical welding (using, e.g., solvents, etc.). In addition, although it may be preferred that the entire surface of each elastic component that faces an anchor be attached to the anchor, in some embodiments, only a portion or portions of the surface of the elastic component may be attached to the anchor.

Methods of transferring the elastomeric polymeric material of the elastic component 20 may be accomplished using forming tools, doctor blades, and methods similar to those described in, e.g., U.S. Patent Application Publication No. U.S. 2003/0087059 A1, filed 5 Nov. 2001 and titled COMPOSITE WEBS WITH DISCRETE ELASTIC POLYMERIC REGIONS, U.S. patent application Ser. No. 10/387, 699, filed Mar. 13, 2003, and titled POLYMER TRANSFER APPARATUS, METHODS, AND COMPOSITE WEBS; and U.S. patent application Ser. No. 10/744,141, filed Dec. 22, 2003, and titled COMPOSITE WEBS AND CLOSURE SYSTEMS. Some other potentially suitable methods of manufacturing composite webs according to the present invention are described herein in connection with FIGS. 7 & 8.

Although FIG. 1 depicts only one elastic composite article, it should be understood that the substrate 10 may preferably include more than one elastic composite structure on the surface 12. Furthermore, although the one depicted elastic composite structure is attached to surface 12 of the substrate 10, it should be understood that one or more elastic composite structures may be located on both major surfaces 12 and 14 of the substrate 10. The one or more elastic composite structures may cover any desired portion of the surfaces 12 and/or 14 of the substrate 10 on which they are positioned. For example, the elastic composite structures may cover all or only a portion of the one or both major surfaces of the substrate 10.

The elastic composite structures on composite webs of the present invention may be uniformly spaced over the surface of the substrate in a regular, repeating pattern (in both the x and y directions) or the spacing and arrangement of elastic composite structures may be non-uniform if so desired. Furthermore, the pattern in which the elastic composite structures are arranged may be irregular.

In other variations, portions of the composite webs manufactured in accordance with the present invention may include uniformly-spaced elastic composite structures, while other portions of the same composite web may be free of any elastic composite structures. In yet another alternative, portions of a composite web manufactured in accordance with the present invention may include uniformly spaced elastic composite structures, while other portions of the same composite web may include elastic composite structures that are arranged in non-uniformly spaced patterns. Further, different portions of a composite web manufactured according to the present invention may include different sets of elastic composite structures that are both uniformly spaced in repeating patterns that are different from each other.

The elastic composite structures may be provided in any desired shape, e.g., squares, rectangles, hexagons, etc. The shapes may or may not be in the form of recognized geometric shapes, but may be randomly formed with irregular perimeters. In addition, the shapes may not necessarily be solid figures, but may include islands formed within the shape in which none of the polymeric material on the forming tool is transferred.

Figure 2:
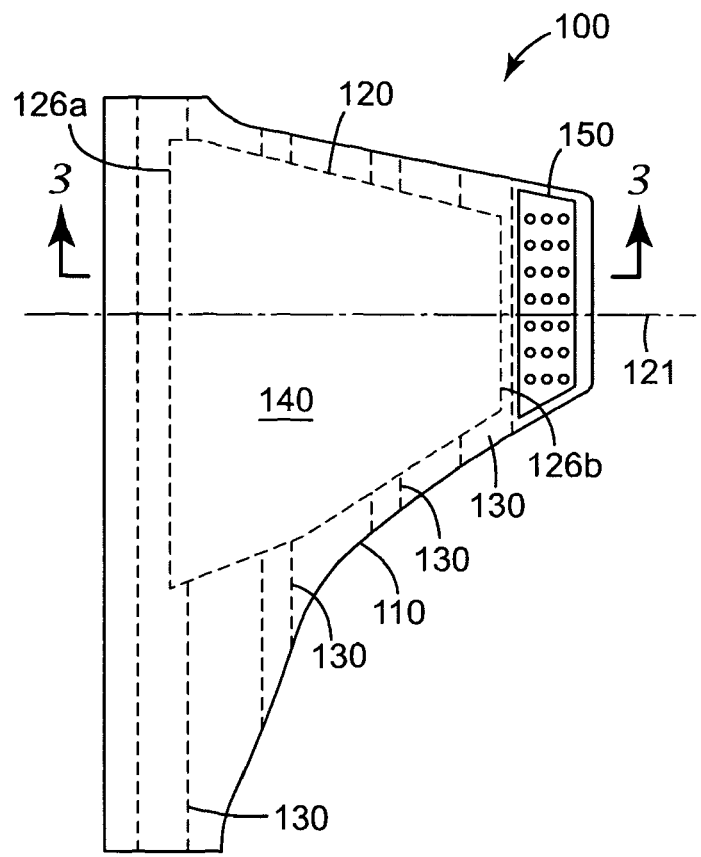
FIG. 2 is a plan view of one exemplary composite article according to the present invention.
Figure 3:
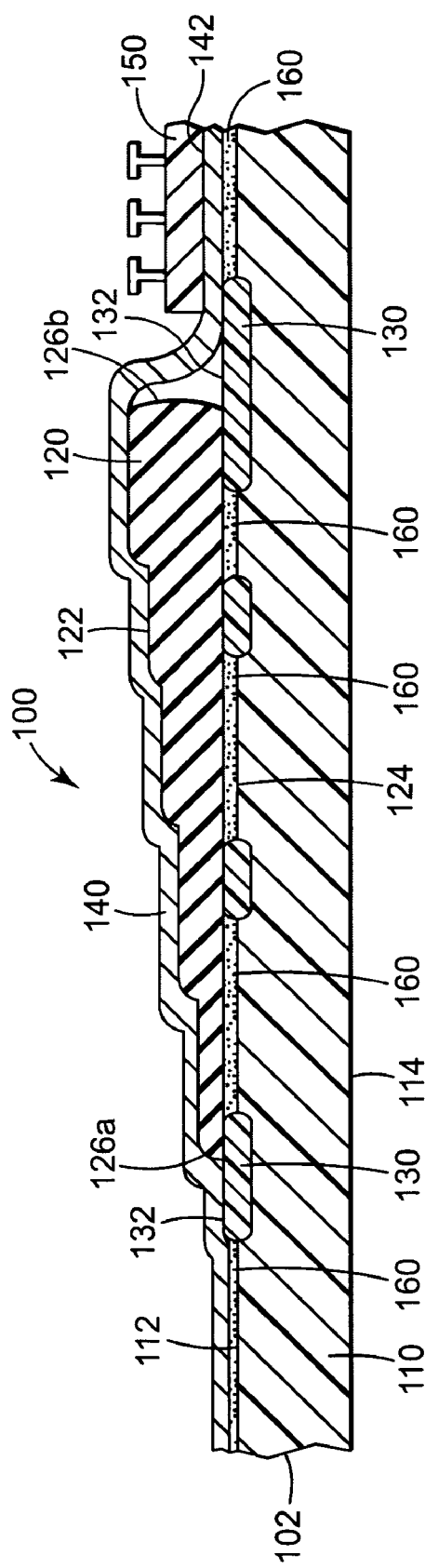
FIG. 3 is a cross-sectional view of the composite article of FIG. 2 taken along line 3-3 in FIG. 2.

FIGS. 2 & 3 depict a second embodiment of the present invention in the form of one exemplary composite article 100 that includes an end 102 opposite a fastener component 150.

The depicted exemplary composite article 100 may be used as, e.g., a closure tab for, e.g., a diaper or other garment, article, etc.

The composite article 100 includes a base substrate 110 and a cover 140, with the elastic composite structure being located between the base substrate 110 and the cover 140. The elastic composite structure includes anchors 130 and elastic component 120 attached to the anchors 130 by any of the suitable techniques described herein for attaching the elastic components to the anchors in elastic composite structures of the present invention. The elastic component 120 and those portions of the anchors 130 not covered by the elastic component 120 are depicted in broken lines in FIG. 2 because they would otherwise be hidden by the cover 140.

The fastener component 150 depicted in FIGS. 2 & 3 is in the form of a mechanical fastener, although it should be understood that the fastener component 150 may be provided in any desired form, e.g., the fastener component 150 may be an area of pressure sensitive adhesive, non-tacky cohesive material, etc. Furthermore, if the fastener component 150 is in the form of a mechanical fastener, it may be any suitable mechanical fastener such as, e.g., hook structure (for, e.g., hook and loop closure systems), mushroom structure (or any other suitable hermaphroditic fastener system), snap, button, clasp, etc. Examples of some potentially suitable fastener components and closures that may be used in connection with the present invention may be described in, e.g., U.S. Pat. Nos. 3,899,803; 5,983,467; 4,887,339; and 4,183,121.

The fastener component 150 may be manufactured and attached to the composite article 100 by any suitable technique or combination of techniques. It may be preferred that the fastener component 150 be attached to the surface 142 of the cover substrate 140 that faces away from the base substrate 110. Alternatively, the fastener component 150 could be attached to the surface 114 of base substrate 110. In yet another alternative, fastener components 150 could be attached to both surface 142 of cover 140 and surface 114 of base substrate 110. In still another alternative, the fastener component 150 could be attached to the surface 112 of substrate 110 in an area not covered by the cover substrate 140.

The cover substrate 140 may be attached to the base substrate 110 using any suitable techniques and materials. In the depicted embodiment, a layer of adhesive 160 is located between the cover substrate 140 and the base substrate 110 outside of the area occupied by the elastic composite structure. Although not depicted, the cover substrate 140 itself may include a layer of adhesive or be otherwise attached to surfaces of the elastic composite structure that face away from the base substrate 110. In another alternative, the cover substrate 140 may itself include a layer of adhesive facing the base substrate 110, with no layer of adhesive 160 on the base substrate 110 itself.

Among the other features depicted in FIGS. 2 & 3 are the multiple anchors 130 attached to the surface 112 of the substrate 110. In turn, the elastic component 120 is attached to the upper surfaces 132 of the anchors 130. In addition to the anchors 130 attached to the substrate 110 proximate the outermost edges 126a and 126b of the elastic component 120, the elastic composite structure includes anchors 130 that are located between those found at the outermost edges of the elastic component 120. Such intermediate anchors 130 may be provided to serve one or more different functions. For example, the intermediate anchors may more securely attach the elastic component 120 to the substrate 110. Alternatively, the intermediate anchors may distribute the forces generated between the elastic component 120 and the anchors 130 during elongation over a larger area. In another alternative, the intermediate anchors 130 may be used to distribute elongation forces over more locations for both the substrate 110 and the elastic component 120.

Another optional feature illustrated in FIGS. 2 & 3 are changes in the width of the elastic component 120 as measured transverse to an axis 121 extending between edges 126a and 126b (see FIG. 2) and changes in the thickness of the elastic component 120 as measured in a direction normal to the surface 112 of the substrate 110. It may be preferred, for example, that the elastic component 120 be thicker in those areas where it is narrower in width as seen in FIGS. 2 & 3. One potential advantage of such a construction is that the elastic recovery forces generated during elongation of the elastic component 120 may be more uniform along axis 121 (particularly if the elastic recovery forces generated within the elastic component are bulk-dependent). In other alternate constructions, the thickest areas of the elastic component 120 may be located somewhere other than the outer edges of the elastic component 120, e.g., the center, etc.

Although the thickness changes in the elastic component 120 are depicted as generally step-wise while moving along axis 121, it should be understood that the thickness of the elastic component 120 may change in any suitable manner, e.g., linearly, etc.

Still another optional feature depicted in FIG. 3 is the layer of adhesive 160 on the surface 112 of the base substrate 110. The adhesive 160 may take any suitable form, e.g., pressure sensitive adhesives, pressure-activated adhesives, heat activated adhesives, hot melt adhesives, epoxies, non-tacky cohesive materials, etc. The adhesive 160 may be provided primarily to attach the cover substrate 140 to the base substrate 110 or it may be useful in retaining the surface 112 of the base substrate 110 proximate the lower surface 124 of the elastic component 120.

The adhesive 160 may preferably be applied to the surface 112 of the substrate before the anchors 130 are attached. In such a construction, the anchors 130 may be attached in areas that are free of the adhesive 160. Alternatively, the anchors 130 may be applied over the adhesive layer 160 by a technique that results in sublimation or displacement of the adhesive (particularly if the polymeric material used for the anchors is at an elevated temperature).

Although the adhesive 160 is depicted as being located continuously over the surface 112 of the base substrate 110 (except where displaced by anchors 130), in some embodiments, the adhesive may be provided discontinuously such that areas of the substrate 110 are free of adhesive 160. In such embodiments, the cover 140 may be attached in a discontinuous manner to the substrate 110. Discontinuous attachment of the cover 140 may, e.g., enhance flexibility of the composite web.

Figure 4:
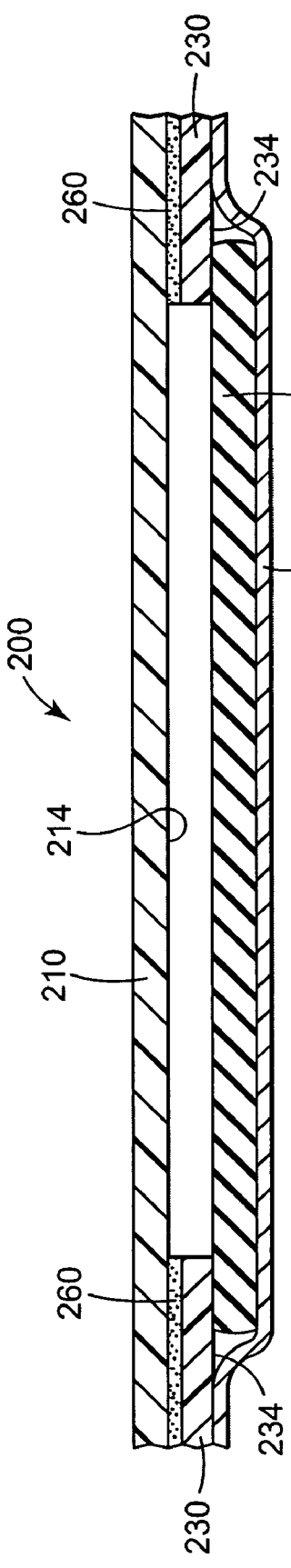
FIG. 4 is a cross-sectional view of another exemplary composite web according to the present invention.

FIG. 4 depicts another alternative exemplary embodiment of an elastic composite structure according to the present invention. The elastic composite structure includes an elastic component 220 attached to anchors 230 that are, in turn, attached to the surface 214 of substrate 210. In many respects, the elastic composite structure of FIG. 4 is similar to the elastic composite structures described above with respect to FIGS. 1-3. One difference, however, is that the anchors 230 are attached to the surface 214 of the substrate 210 using adhesive 260.

For elastic composite structures that are attached using anchors 230 adhered to the substrate 210 using, e.g., adhesive 260, it may be preferred that the anchors 230 do not exhibit any significant elongation when the elastic component 220 is stretched or elongated as described herein. It may further be preferred that the inelastic anchors 230 also reduce or prevent extensibility or elongation of those portions of the substrate 210 to which the anchors 230 are attached using adhesive 260. By providing anchors 230 that are, themselves, substantially inelastic, the issues of adhesive creep discussed above with respect to adhesive attachment of elastic components to substrates may be limited or avoided entirely. In some instances, it may be preferred that the anchors be formed of inelastic polymeric material.

Another optional feature depicted in FIG. 4 is a cover 240 located over the elastic composite structure. In a variation of the cover 140 described above with respect to FIGS. 2 & 3, the cover 240 is attached directly to the surface 234 of the anchors 230 where the anchors 230 extend out from the elastic component 220. The cover 240 in such an embodiment may be any suitable substrate among those, e.g., described herein. Attachment of the cover 240 to the anchors 230 may be any suitable method such as, e.g., thermal attachment (e.g., heat sealing, spot welding, extrusion bonding, etc.) ultrasonic attachment, chemical welding (using, e.g., solvents, etc.), adhesives, etc. The cover 240 may be attached continuously or discontinuously (i.e., in specific areas separated by areas where the cover is not attached).

Figure 5:
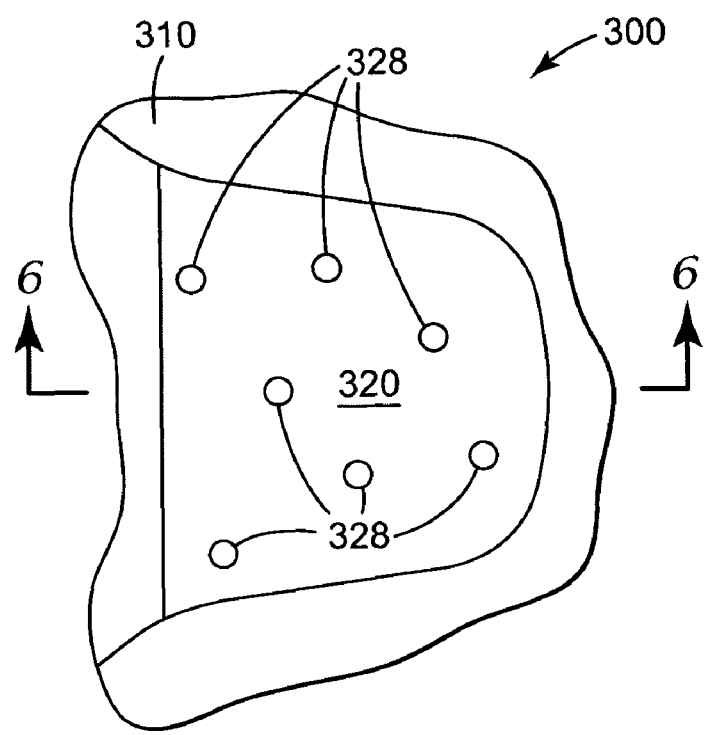
FIG. 5 is a plan view of another exemplary composite article according to the present invention.
Figure 6:
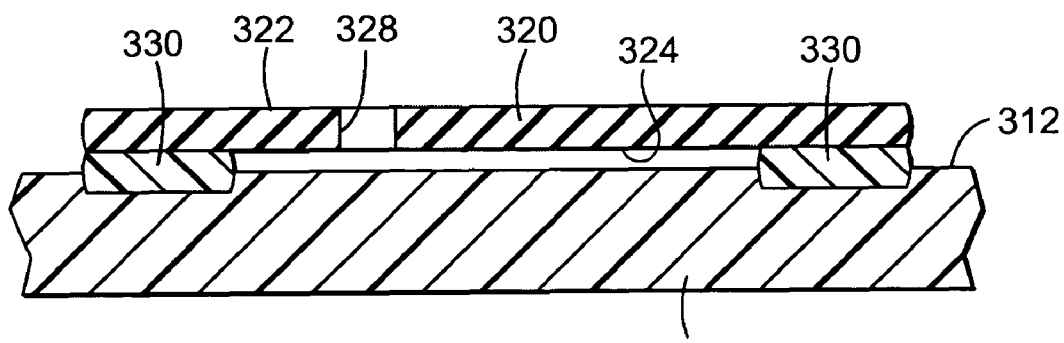
FIG. 6 is a cross-sectional view of the composite article of FIG. 5 taken along line 6-6 in FIG. 5.

FIGS. 5 & 6 depict another alternative embodiment of an article according to the present invention. The article 300 includes a substrate 310 with an elastic composite structure attached to surface 312 of the substrate 310. The elastic composite structure includes anchors 330 and an elastic component 320 attached to the anchors 330. In many respects, the elastic composite structure of FIGS. 5 & 6 is similar to those described in FIGS. 1-3. One difference is, however, that the elastic component 320 includes one or more voids 328 that are formed through the elastic component 320 from the surface 322 to surface 324.

The voids 328 may provide one or more different functions. For example, the voids 328 may enhance breathability of the article 300 in the area of the substrate 310 occupied by the elastic composite structure by, e.g., allowing materials to pass through the voids 328. Another potential function that may be performed by the voids 328 is to adjust the elastic recovery forces exhibited by the elastic component 320 in response to tension over the elastic component 320. The recovery forces may be adjusted by voids 328 because the elastic polymeric material that would have been present in the voids 328 is not available to contribute to the elastic recovery forces.

The voids 328 may be provided in the elastic component 320 at the time the elastic component 320 is formed or constructed using, e.g., islands or other structures located within a depression on a forming tool (see, e.g., U.S. Patent Publication No. U.S. 2003/0087098 A1). Another alternative for constructing the elastic component 320 with voids 328 is to form the voids 328 in what was otherwise a void-free elastic component 320. The voids may be formed by, e.g., punching, die cutting, laser energy, water jets, etc.

Figure 7:
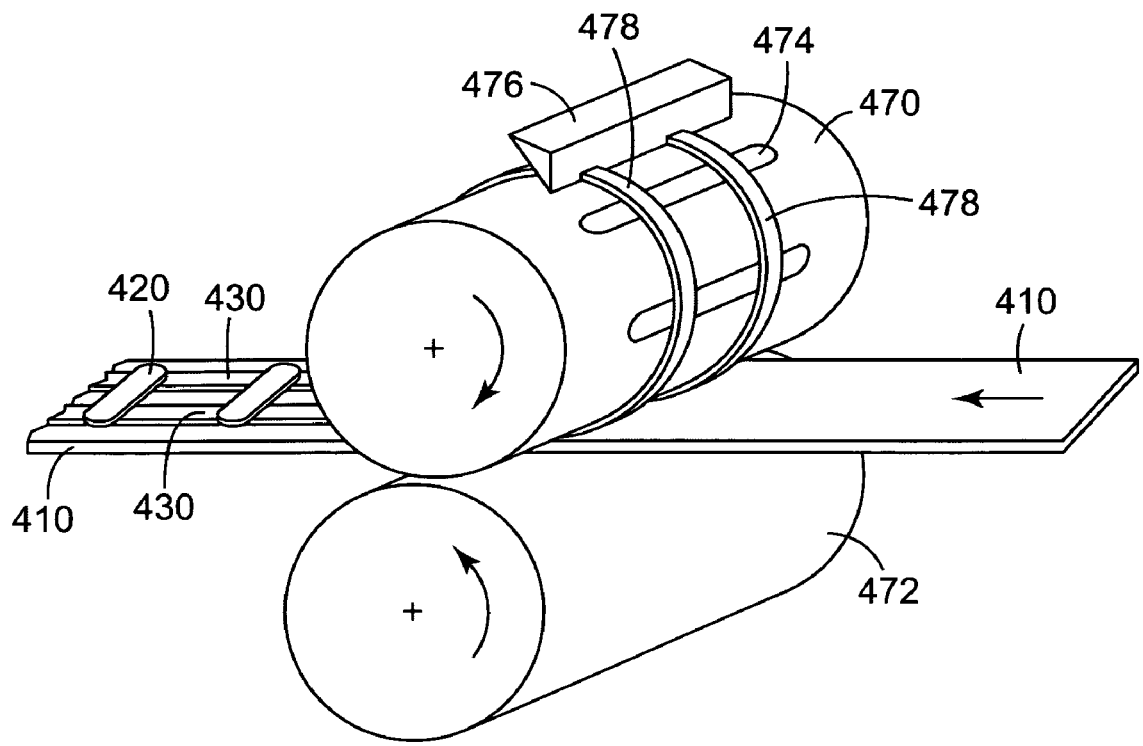
FIG. 7 depicts on exemplary method of manufacturing a composite web according to the present invention.

FIG. 7 depicts one exemplary embodiment of one potentially useful process for manufacturing a composite web according to the present invention. The method includes the use of a roll 470 as a forming tool. A backup roll 472 is provided to form a nip with roll 470. A substrate 410 is directed into the nip formed by rolls 470 and 472.

The forming roll 470 includes depressions 474 that may be used to receive a molten elastomeric polymeric composition as described in, e.g., many of the patent applications cited herein. The apparatus used to deliver the elastomeric polymeric composition to depressions 474 is not, however depicted in FIG. 7. Although the elastomeric polymeric depressions 474 and resulting elastic components 420 are depicted in the form of separate, discrete features or articles, in some embodiments, the elastomeric polymeric material may preferably be formed into an article (preferably continuous) such as, e.g., mesh or netting (with openings formed therethrough), a continuous film, a traversing strand or strands, etc. If a forming tool (such as, e.g., a roll) is used to form such elastic components, it may be preferred that the depressions in the forming tool have the appropriate shape or shapes to form the mesh, netting, film, etc. (or that the apparatus used to deposit the elastomeric polymeric material on the forming tool do so in the desired shape or form).

FIG. 7 does include, however, apparatus to provide anchor polymeric composition 478 on the roll 470, with a portion of the anchor polymeric composition 478 located on the elastomeric polymeric composition in depressions 474 (sometimes referred to herein as the anchor portions of the elastomeric polymeric composition). In the depicted method and apparatus, the anchor polymeric composition is provided in the form of two lines extending along the machine direction as defined by the rotation of rolls 470 and 472. In some instances, the anchor polymeric composition may be limited in coverage, such that the anchor polymeric material is located only on the elastomeric polymeric composition.

Transfer of the elastomeric polymeric composition and the anchor polymeric composition to the substrate 410 occurs within the nip formed by rolls 470 and 472. After passing through the nip, the substrate 410 includes anchors 430 attached to a major surface and elastic components 420 extending between the attached anchors 430 as described herein. After transfer of the elastic components 420 and the anchors 430, the web 410 can be sheeted or otherwise separated to provide composite articles according to the present invention.

Figure 8:
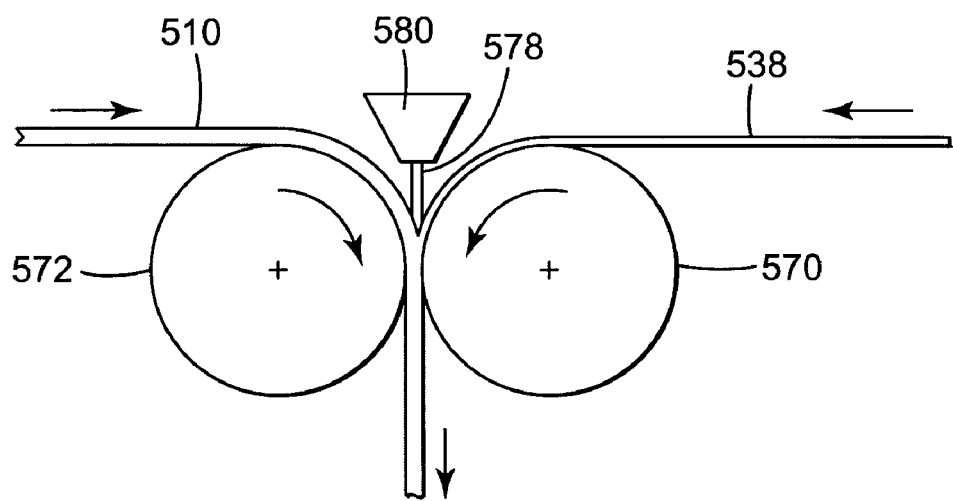
FIG. 8 depicts another exemplary method of manufacturing a composite web according to the present invention.

FIG. 8 depicts another exemplary manufacturing method in which a base substrate 510 and an elastic substrate 538 are directed into a nip formed between rolls 570 and 572. Molten anchor polymeric material 578 is delivered to the nip such that the anchor polymeric material 578 is located between the base substrate 510 and the elastic substrate 538. The anchor polymeric material 578 may be delivered to the nip in two or more separate continuous strands or in discrete masses from a source 580. The source 580 may be, e.g., an extrusion die or other device capable of delivering molten anchor polymeric material 578 in the desired form to the nip.

It is preferred that the anchor polymeric attach to both the base substrate 510 and the elastic substrate 538, with the elastic substrate 538 extending between two or more anchors to form an elastic composite structure in accordance with the present invention. It may be preferred that the base substrate be provided in the form of a nonwoven web, although many other substrates could be used as are described herein. The elastic substrate 538 may also take a variety of forms, e.g., mesh or netting (with openings formed therethrough), a continuous film, a traversing strand or strands, etc. The elastic substrate 538 forms the elastic component in such a structure. The composite web formed by the base substrate 510, elastic substrate 538 and anchor polymeric material 578 can be sheeted or otherwise separated to provide composite articles according to the present invention.

Although two exemplary methods of and apparatus for manufacturing composite webs and articles according to the present invention are depicted in FIGS. 7 & 8, it should be understood that many different methods and apparatus could be used in connection with the present invention. In one variation of the method and apparatus depicted in FIG. 8, for example, the elastic substrate 538 may be formed in-line with the nip formed by rolls 570 and 572. For example, the elastic substrate 538 may be formed directly on roll 570 which then directs the elastic substrate 538 into the nip with roll 572.

Figure 9:
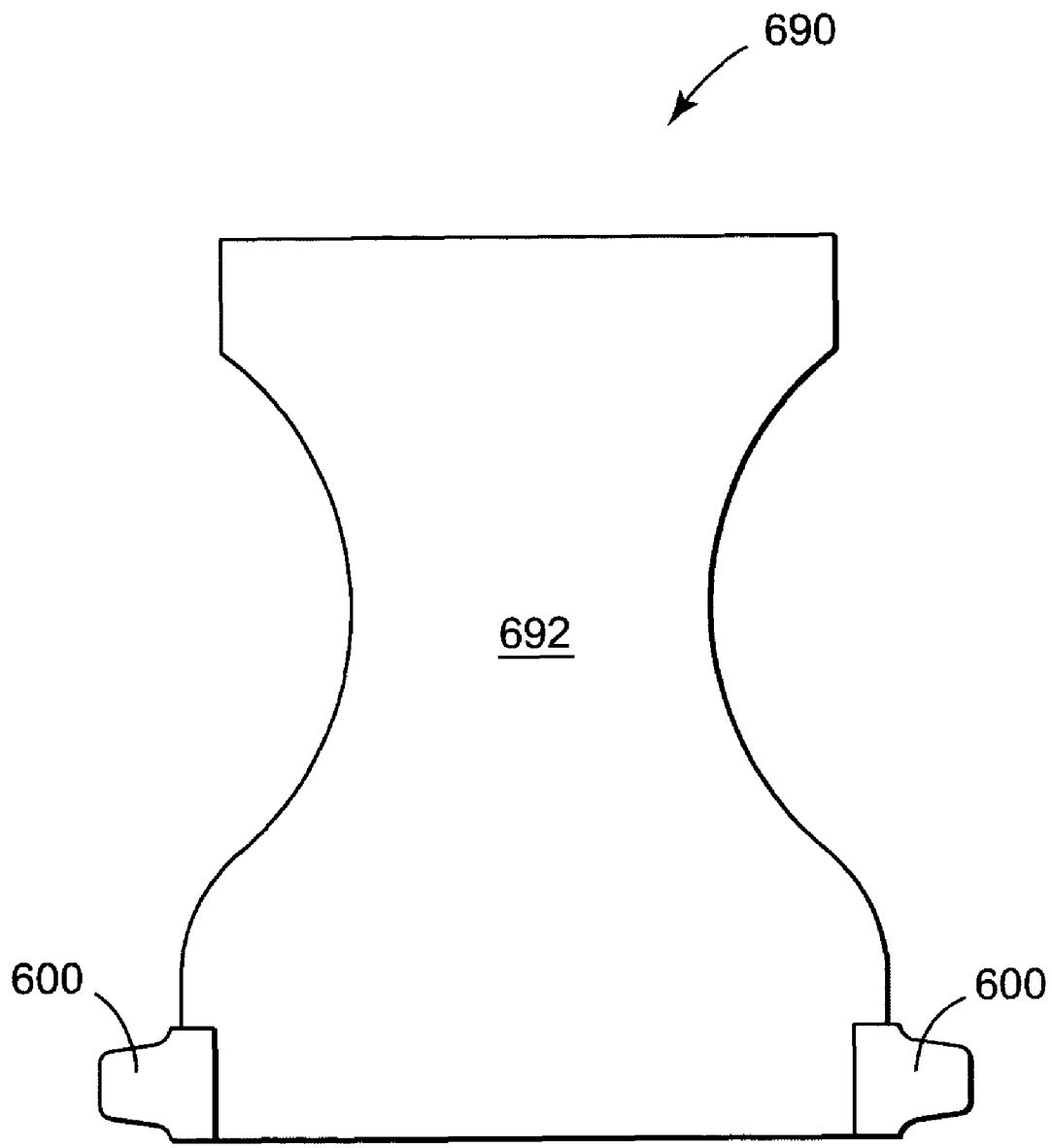
FIG. 9 depicts one exemplary device including one or more elastic composite articles according to the present invention.

Although the elastic composite structures may be used in a wide variety of articles and devices, the elastic composite structures may be used to manufacture closure tabs for fastening garments, incontinence devices (e.g., diapers), etc. FIG. 9 depicts one such device 690 in the form of an incontinence device that includes a chassis 692 to which closure tabs 600 are attached. The closure tabs 600 and/or the chassis 692 itself may be manufactured according to the principles of the present invention to include elastic composite structures. Some incontinence devices may be described in, e.g., U.S. Pat. No. 5,399,219 (Roessler et al.) and U.S. Pat. No. 5,685,873 (Bruemmer et al.).

The following discussions will provide some guidance as to potentially suitable substrates and polymeric materials (both elastic and inelastic) that may be used in composite webs of the present invention.

Substrates

The substrates used in connection with the composite webs of the present invention may have a variety of constructions. For example, the substrates may be a woven material, nonwoven material, knit material, netting, scrim, foam, paper, film, or any other continuous media that can be fed through a nip point. The substrates may have a wide variety of properties, such as extensibility, elasticity, flexibility, conformability, breathability, porosity, stiffness, etc. Further, the substrates may include pleats, corrugations, microcreping, or other deformations from a flat planar sheet configuration. In addition, the substrates used in connection with the present invention may or may not require activation, i.e., elongation or extension before use.

In some instances, the substrates may be manufactured using fibers. As used herein, the term "fiber" includes fibers of indefinite length (e.g., filaments) and fibers of discrete length, e.g., staple fibers. The fibers used in connection with the present invention may be multicomponent fibers. The term "multicomponent fiber" refers to a fiber having at least two distinct longitudinally coextensive structured polymer domains in the fiber cross-section, as opposed to blends where the domains tend to be dispersed, random, or unstructured. The distinct domains may thus be formed of polymers from different polymer classes (e.g., nylon and polypropylene) or be formed of polymers from the same polymer class (e.g., nylon) but which differ in their properties or characteristics. The term "multicomponent fiber" is thus intended to include, but is not limited to, concentric and eccentric sheath-core fiber structures, symmetric and asymmetric side-by-side fiber structures, island-in-sea fiber structures, pie wedge fiber structures, and hollow fibers of these configurations.

It may be preferred that the substrates exhibit some level of extensibility and also, in some instances, elasticity. Extensible webs that may be preferred may have an initial yield tensile force of at least about 50 gm/cm, preferably at least about 100 gm/cm. Further, the extensible webs may preferably be extensible nonwoven webs.

Suitable processes for making a nonwoven web that may be used in connection with the present invention include, but are not limited to, airlaying, spunbond, spunlace, bonded melt blown webs and bonded carded web formation processes. Spunbond nonwoven webs are made by extruding a molten thermoplastic, as filaments from a series of fine die orifices in a spinneret. The diameter of the extruded filaments is rapidly reduced under tension by, for example, by non-eductive or eductive fluid-drawing or other known spunbond mechanisms, such as described in U.S. Pat. No. 4,340,563 (Appel et al.); U.S. Pat. No. 3,692,618 (Dorschner et al.); U.S. Pat. Nos. 3,338,992 and 3,341,394 (Kinney); U.S. Pat. No. 3,276,944 (Levy); U.S. Pat. No. 3,502,538 (Peterson); U.S. Pat. No. 3,502,763 (Hartman) and U.S. Pat. No. 3,542,615 (Dobo et al.). The spunbond web is preferably bonded (point or continuous bonding).

The nonwoven web layer may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation.

Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between 6 to 19 millimeters are separated and entrained in an air supply and then deposited onto a forming screen, often with the assistance of a vacuum supply. The randomly deposited fibers are then bonded to one another using, for example, hot air or a spray adhesive.

Meltblown nonwoven webs may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, meltblown webs must be further bonded such as by through air bonding, heat or ultrasonic bonding as described above.

A web can be made extensible by skip slitting as is disclosed in, e.g., International Publication No. WO 96/10481 (Abuto et al.). If an elastic, extensible web is desired, the slits are discontinuous and are generally cut on the web prior to the web being attached to any elastic component. Although more difficult, it is also possible to create slits in the nonelastic web layer after the nonelastic web is laminated to the elastic web. At least a portion of the slits in the nonelastic web should be generally perpendicular (or have a substantial perpendicular vector) to the intended direction of extensibility or elasticity (the at least first direction) of the elastic web layer. By generally perpendicular it is meant that the angle between the longitudinal axis of the chosen slit or slits and the direction of extensibility is between 60 and 120 degrees. A sufficient number of the described slits are generally perpendicular such that the overall laminate is elastic. The provision of slits in two directions is advantageous when the elastic laminate is intended to be elastic in at least two different directions.

A nonwoven web used in connection with the present invention can also be a necked or reversibly necked nonwoven web as described in U.S. Pat. Nos. 4,965,122; 4,981,747; 5,114,781; 5,116,662; and 5,226,992 (all to Morman). In these embodiments the nonwoven web is elongated in a direction perpendicular to the desired direction of extensibility. When the nonwoven web is set in this elongated condition, it will have stretch and recovery properties in the direction of extensibility.

The substrates used in connection with the present invention may preferably exhibit some porosity on one or both of the major surfaces of the substrate such that when a molten polymeric material is transferred to one of the major surfaces of the substrate, a mechanical bond may be formed between the molten polymeric material and the substrate as the molten polymeric material infiltrates and/or encapsulates a portion of the porous surface of the substrate. As used in connection with the present invention, the term "porous" includes both structures that include voids formed therein, as well as structures formed of a collection of fibers (e.g., woven, nonwoven, knit, etc.) that allow for the infiltration of molten polymeric material into the interstices between fibers. If the porous surface includes fibers, the polymeric material may preferably encapsulate fibers or portions of fibers on the surface of the substrate.

If the substrate is not porous (e.g., is a film such as a polymeric film), but is made with a thermoplastic polymeric composition that has a melt processing temperature sufficiently low relative to the temperature of the molten polymeric material in the depressions, then attachment of the elastic composite structures to the substrate may be achieved by intermixing (e.g., surface mixing as seen in, e.g., fusion bonding or heat sealing of, e.g., polymeric materials) of the thermoplastic polymeric compositions of the substrate with the polymeric material of the elastic composite structures. To attach elastic composite structures in accordance with the present invention on substrates formed of thermoplastic polymeric compositions themselves, the substrate thermoplastic polymeric composition may preferably have a melt processing temperature that is at or below the melt processing temperature of the polymeric materials of the elastic composite structures attached to the substrate (e.g., the inelastic polymeric material of the anchors).

The type and construction of the material or materials in the substrate should preferably be considered when selecting an appropriate substrate to which a molten thermoplastic composition is applied. For example, the substrate should preferably have sufficient internal strength such that it does not fall apart during the process. Preferably, the substrate has sufficient strength in the machine direction under process conditions to remove it intact from the forming tool.

Although the substrates depicted in the various cross-sectional views of the articles manufactured according to the methods of the present invention are illustrated as single layer structures, it should be understood that the substrates may be of single or multi-layer construction. If a multi-layer construction is used, it will be understood that the various layers may have the same or different properties, constructions, etc. Some of these variations may be as described in, for example, pending U.S. patent application Ser. No. 09/257,447, entitled WEB HAVING DISCRETE STEM REGIONS, filed on Feb. 25, 1999 (published as International Publication No. WO 00/50229).

Polymeric Materials

The various components of the elastic composite structures of the present invention may be formed of a wide variety of different polymeric materials. Some examples of polymeric materials that may be used in connection with the present invention include, but are not limited to, polyurethanes, polyolefins (e.g., polypropylenes, polyethylenes, etc.), polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons, fluorocarbons, etc. Suitable polymeric materials may generally have a melt flow index of 5-200 grams/10 minutes measured at the appropriate conditions for the polymer as specified in ASTM D 1238. Furthermore, in some instances, one or more of the polymeric materials used to construct the elastic composite structures may be, e.g., a thermoplastic hot melt adhesive.

The polymeric materials of the present invention may include either or both of nonelastomeric or elastomeric polymeric materials (preferably thermoplastic polymeric materials). A nonelastomeric polymer is one that is melt processable and that returns to its original condition or near its original condition upon cooling (after melt processing) and which does not exhibit elastomeric properties at ambient conditions (e.g., room temperature and pressure). As used in connection with the present invention, "nonelastomeric" means that the material will not substantially resume its original shape after being stretched. Further, the nonelastomeric polymers may preferably sustain permanent set following deformation and relaxation, which set is preferably at least about 20 percent or more, and more preferably at least about 30 percent or more of the original length at moderate elongation, e.g., about 50% (for those materials that can even be stretched up to 50% without fracture or other failure).

An elastomeric (or elastic) polymeric material is one that is melt processable and that returns to its original condition or near its original condition upon cooling (after melt processing) and that exhibits elastomeric properties at ambient conditions (e.g., room temperature and pressure). As used in connection with the present invention, "elastomeric" means that the material will substantially resume its original shape after being stretched. Further, the elastomeric polymeric materials may preferably sustain only small permanent set following deformation and relaxation which set is preferably no greater than about 30 percent and more preferably no greater than about 20 percent of the original length at moderate elongation, e.g., about 50%. The elastomeric polymeric materials of the present invention can be both pure elastomers and blends with an elastomeric phase or content that will still exhibit substantial elastomeric properties at room temperature. U.S. Pat. No. 5,501,679 (Krueger et al.) provides some further discussion regarding elastomeric materials that may be considered for use in connection with the present invention.

The elastomeric polymeric materials can include one or more polymers. For example, the polymeric material could be a blend with an elastomeric phase such that the polymeric material exhibits elastomeric properties at room temperature. Suitable elastomeric thermoplastic polymer compositions may include block copolymers such as conventional A-B or A-B-A block copolymers (e.g., styrene-isoprene-styrene, styrene-butadiene-styrene, styrene-ethylene-butylene-styrene block copolymers), elastomeric polyurethanes, olefinic elastomers, particularly elastomeric ethylene copolymers (e.g., ethylene vinyl acetates, ethylene/octene copolymer elastomers, ethylene/propylene/diene terpolymer elastomers), as well as mixtures of these with each other, with other elastomeric polymers, or with nonelastomeric polymeric materials.

The polymeric materials used in connection with the present invention can also be combined with various additives for desired effect. These include, for example, fillers, viscosity reducing agents, plasticizers, tackifiers, colorants (e.g., dyes or pigments), antioxidants, antistatic agents, bonding aids, antiblocking agents, slip agents, stabilizers (e.g., thermal and ultraviolet), foaming agents, microspheres, glass bubbles, reinforcing fibers (e.g., microfibers), internal release agents, thermally conductive particles, electrically conductive particles, and the like. The amounts of such materials that can be useful in the thermoplastic compositions can be readily determined by those skilled in the art of processing and using such materials.

As used herein and in the appended claims, the singular forms "a," "and," and "the" include plural referents unless the context clearly dictates otherwise. Thus, for example, reference to "an elastic composite structure" includes a plurality of elastic composite structures and reference to "the elastic component" includes reference to one or more elastic components and equivalents thereof known to those skilled in the art. Similarly, where two components or features are recited, it should be understood that more than two components or features are also included unless the context clearly dictates otherwise (e.g., "two anchors" includes three or more anchors).

All references and publications identified herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of manufacturing a composite web, the method comprising:
    delivering molten elastomeric polymeric composition onto a forming tool;
    maintaining the forming tool at a roll temperature that is below a melt processing temperature of the elastomeric polymeric composition;
    depositing a molten anchor polymeric composition on at least two portions of the elastomeric polymeric composition;
    transferring the anchor polymeric composition to a first major surface of a base substrate, wherein the transferring comprises contacting the first major surface of the substrate with the anchor polymeric composition; and
    separating the elastomeric polymeric composition from the forming tool after the transferring;
    wherein a composite web is formed that comprises one or more elastic composite structures on the first major surface of the base substrate, wherein each of the elastic composite structures comprises an elastic component attached to at least two anchors, wherein the anchors comprise the anchor polymeric composition and wherein the elastic component comprises the elastomeric polymeric composition.

2. A method according to claim 1, wherein the anchor polymeric composition comprises an inelastic polymeric composition.

3. A method according to claim 1, wherein each anchor of the at least two anchors formed by the anchor polymeric composition exhibits elastic recovery of 50% or less after elongation along any in-plane direction over the first major surface of the base substrate.

4. A method according to claim 1, wherein each anchor of the at least two anchors formed by the anchor polymeric composition exhibits elastic recovery of 30% or less after elongation along any in-plane direction over the first major surface of the base substrate.

5. A method according to claim 1, wherein each anchor of the at least two anchors formed by the anchor polymeric composition exhibits elastic recovery of 10% or less after elongation along any in-plane direction over the first major surface of the base substrate.

6. A method according to claim 1, wherein, when the elastic composite structure is elongated in a stretch direction extending through the at least two anchors such that the elastic component exhibits 50% elongation as measured along the stretch direction, each anchor of the two anchors exhibits 10% or less elongation as measured along the stretch direction.

7. A method according to claim 1, wherein, when the elastic composite structure is elongated in a stretch direction extending through the at least two anchors such that the elastic component exhibits 25% elongation as measured along the stretch direction, each anchor of the two anchors exhibits 2% or less elongation as measured along the stretch direction.

8. A method according to claim 1, wherein delivering the molten elastomeric polymeric composition onto an exterior surface of a forming tool comprises wiping the molten elastomeric polymeric composition on the exterior surface of the forming tool such that at least some of the molten elastomeric polymeric composition enters the one or more depressions in the exterior surface of the forming tool.

9. A method according to claim 8, wherein at least a portion of the molten anchor polymeric composition is located on a portion of the elastomeric polymeric composition in the one or more depressions.

10. A method according to claim 8, wherein the elastomeric polymeric composition in the one or more depressions is below its melt processing temperature when the anchor polymeric composition located on the elastomeric polymeric composition contacts the first major surface of the base substrate during the transferring.

11. A method according to claim 1, wherein at least a portion of the elastomeric polymeric composition on the exterior surface of the forming tool is below its melt processing temperature when the anchor polymeric composition located on the elastomeric polymeric composition contacts the first major surface of the base substrate during the transferring.

12. A method according to claim 1, wherein at least a portion of the anchor polymeric composition is at or above its melt processing temperature when it contacts the first major surface of the base substrate during the transferring.

13. A method according to claim 1, wherein the first major surface of the base substrate comprises a porous surface, and wherein a portion of the anchor polymeric composition infiltrates the porous surface after the transferring.

14. A method according to claim 13, wherein the porous surface comprises fibers, and further wherein the anchor polymeric composition encapsulates at least a portion of at least some of the fibers after the transferring.

15. A method according to claim 1, wherein the first major surface of the base substrate comprises fibers, and further wherein the anchor polymeric composition encapsulates at least a portion of at least some of the fibers after the transferring.

16. A method according to claim 1, wherein the first major surface of the base substrate comprises polymeric material with a melt processing temperature at or below a melt processing temperature of the anchor polymeric composition.

17. A method according to claim 1, wherein the elastic component of the elastic composite structure is not attached to the base substrate between the two anchors.

18. A method according to claim 1, further comprising adhesively attaching the elastic component of the elastic composite structure to the base substrate between the anchors.

19. A method according to claim 1, wherein the elastic component comprises one or more openings formed therethrough.

20. A method according to claim 1, wherein the elastic component comprises a first end and a second end defining a longitudinal axis therebetween, and wherein the elastic component comprises a thickness measured normal to the first major surface of the base substrate, and further wherein the thickness of the elastic component is different at selected locations along the longitudinal axis.

21. A method according to claim 20, wherein the thickness of the elastic component is greater proximate the first end than the thickness of the elastic component proximate the second end.

22. A method according to claim 1, wherein the elastic component comprises a first end and a second end defining a longitudinal axis therebetween, and wherein the elastic component comprises a width measured generally transverse to the longitudinal axis and along an in-plane direction on the first major surface of the base substrate, and further wherein the width of the elastic component is different at selected locations along the longitudinal axis.

23. A method according to claim 22, wherein the width of the elastic component is greater proximate the second end than the width of the elastic component proximate the first end.

24. A method according to claim 22, wherein the elastic component comprises a thickness measured normal to the first major surface of the base substrate, and further wherein the thickness of the elastic component is different at selected locations along the longitudinal axis.

25. A method according to claim 24, wherein the thickness of the elastic component is greater proximate the first end than the thickness of the elastic component proximate the second end.

26. A method according to claim 25, wherein the thickness of the elastic component is greater proximate the second end than the thickness of the elastic component proximate the first end.

27. A method according to claim 1, further comprising attaching a cover substrate over the one or more elastic composite structures on the first major surface of the base substrate, wherein the one or more elastic composite structures are located between the base substrate and the cover substrate.

28. A method according to claim 27, wherein the cover substrate is attached to the anchors.

29. A method according to claim 25, wherein the cover substrate is adhesively attached over the one or more elastic composite articles and the first major surface of the base substrate.

30. A method of manufacturing a composite web, the method comprising:
providing a forming tool comprising an exterior surface that comprises one or more depressions formed therein;
delivering a molten elastomeric polymeric composition onto an exterior surface of the forming tool;
maintaining the exterior surface of the forming tool at a roll temperature that is below a melt processing temperature of the elastomeric polymeric composition;
wiping the molten elastomeric polymeric composition on the exterior surface of the forming tool, wherein at least some of the molten elastomeric polymeric composition enters one or more depressions in the exterior surface of the forming tool;

depositing molten anchor polymeric material on at least a portion of the elastomeric polymeric composition, wherein at least a portion of the molten anchor polymeric composition is located on the elastomeric polymeric composition in the one or more depressions;

transferring the anchor polymeric composition to a first major surface of a base substrate, wherein the transferring comprises contacting the first major surface of the substrate with the anchor polymeric composition, wherein the first major surface of the base substrate comprises a porous surface, and wherein a portion of the anchor polymeric composition infiltrates the porous surface after the transferring; and separating the elastomeric polymeric composition in the one or more depressions and the anchor polymeric composition from the forming tool after the transferring;

wherein a composite web is formed that comprises one or more elastic composite structures on the first major surface of the base substrate, wherein each of the elastic composite structures comprises an elastic component attached to at least two anchors, wherein the anchors comprise the anchor polymeric composition and wherein the elastic component comprises the elastomeric polymeric composition.

31. A method of manufacturing a composite web, the method comprising:

delivering molten elastomeric polymeric composition onto a forming tool;

maintaining the forming tool at a roll temperature that is below a melt processing temperature of the elastomeric polymeric composition;

depositing molten anchor polymeric composition on at least a portion of the elastomeric polymeric composition;

transferring a portion of the anchor polymeric composition to a first major surface of a base substrate, wherein the transferring comprises contacting the first major surface of the substrate with the anchor polymeric composition, and wherein the transferred anchor polymeric composition forms anchors attached to the first major surface of the base substrate; and separating the elastomeric polymeric composition from the forming tool after the transferring, wherein the separated elastomeric polymeric composition forms one or more elastic components;

wherein a composite web is formed after the transferring and the separating, with the composite web comprising one or more elastic composite structures on the first major surface of the base substrate, wherein at least one of the elastic composite structures comprises one of the elastic components attached to at least two of the anchors, and further wherein the elastic component is not attached to the first major surface of the base substrate between the two anchors.

32. A method according to claim 31, wherein each anchor of the at least two anchors formed by the anchor polymeric composition exhibits elastic recovery of 50% or less after elongation along any in-plane direction over the first major surface of the base substrate.

33. A method according to claim 31, wherein, when the elastic composite structure is elongated in a stretch direction extending through the at least two anchors such that the elastic component exhibits 50% elongation as measured along the direction, each anchor of the two anchors exhibits 10% or less elongation as measured along the stretch direction.

34. A method according to claim 31, wherein delivering the molten elastomeric polymeric composition onto an exterior surface of a forming tool comprises wiping the molten elastomeric polymeric composition such that at least some of the molten elastomeric polymeric composition enters one or more depressions in the exterior surface of the forming tool.

35. A method according to claim 34, wherein at least a portion of the molten anchor polymeric composition is located on a portion of the elastomeric polymeric composition in the one or more depressions.

36. A method according to claim 31, wherein at least a portion of the elastomeric polymeric composition on the exterior surface of the forming tool is below its melt processing temperature when the anchor polymeric composition located on the elastic polymeric composition contacts the first major surface of the base substrate during the transferring.

37. A method according to claim 31, wherein at least a portion of the anchor polymeric composition is at or above its melt processing temperature when it contacts the first major surface of the base substrate during the transferring.

38. A method according to claim 31, wherein the first major surface of the base substrate comprises a porous surface, and wherein a portion of the anchor polymeric composition infiltrates the porous surface after the transferring.

39. A method according to claim 31, wherein the first major surface of the base substrate comprises fibers, and further wherein the anchor polymeric composition encapsulates at least a portion of at least some of the fibers after the transferring.

40. A method according to claim 31, wherein the first major surface of the base substrate comprises polymeric material with a melt processing temperature at or below a melt processing temperature of the anchor polymeric composition.

41. A method according to claim 31, wherein the elastic component comprises one or more openings formed therethrough.

42. A method according to claim 31, wherein the elastic component comprises a first end and a second end defining a longitudinal axis therebetween, and wherein the elastic component comprises a thickness measured normal to the first major surface of the base substrate, and further wherein the thickness of the elastic component is different at selected locations along the longitudinal axis.

43. A method according to claim 31, wherein the elastic component comprises a first end and a second end defining a longitudinal axis therebetween, and wherein the elastic component comprises a width measured generally transverse to the longitudinal axis and along an in-plane direction on the first major surface of the base substrate, and further wherein the width of the elastic component is different at selected locations along the longitudinal axis.

44. A method according to claim 31, further comprising attaching a cover substrate over the one or more elastic composite structures on the first major surface of the base substrate, wherein the one or more elastic composite structures are located between the base substrate and the cover substrate.

45. A method according to claim 44, wherein the cover substrate is adhesively attached over the one or more elastic composite articles and the first major surface of the base substrate.

46. A method of manufacturing a composite web, the method comprising:

delivering molten elastomeric polymeric composition onto a forming tool;

maintaining the forming tool at a roll temperature that is below a melt processing temperature of the elastomeric polymeric composition;

depositing molten anchor polymeric composition on at least a portion of the elastomeric polymeric composition;

transferring the anchor polymeric composition to a first major surface of a base substrate, wherein the transferring comprises contacting the first major surface of the substrate with the anchor polymeric composition, and wherein the transferred anchor polymeric composition forms anchors attached to the first major surface of the base substrate;

separating the elastomeric polymeric composition from the forming tool after the transferring, wherein the separated elastomeric polymeric composition forms one or more elastic components; and providing adhesive on at least a portion of the first major surface of the base substrate;

wherein a composite web is formed after the transferring and the separating, with the composite web comprising one or more elastic composite structures on the first major surface of the base substrate, wherein at least one of the elastic composite structures comprises one of the elastic components attached to and extending between at least two of the anchors, and further wherein the elastic component is adhesively attached to the first major surface of the substrate between the anchors.

47. A method according to claim 46, wherein each anchor of the at least two anchors formed by the anchor polymeric composition exhibits elastic recovery of 50% or less after elongation along any in-plane direction over the first major surface of the base substrate.

48. A method according to claim 46, wherein, when the elastic composite structure is elongated in a stretch direction extending through the at least two anchors such that the elastic component exhibits 50% elongation as measured along the direction, each anchor of the two anchors exhibits 10% or less elongation as measured along the stretch direction.

49. A method according to claim 46, wherein delivering the molten elastomeric polymeric composition onto an exterior surface of a forming tool comprises wiping the molten elastomeric polymeric composition such that at least some of the molten elastomeric polymeric composition enters one or more depressions in the exterior surface of the forming tool.

50. A method according to claim 49, wherein at least a portion of the molten anchor polymeric composition is located on a portion of the elastomeric polymeric composition in the one or more depressions.

51. A method according to claim 46, wherein at least a portion of the elastomeric polymeric composition on the exterior surface of the forming tool is below its melt processing temperature when the anchor polymeric composition located on the elastomeric polymeric composition contacts the first major surface of the base substrate during the transferring.

52. A method according to claim 46, wherein at least a portion of the anchor polymeric composition is at or above its melt processing temperature when it contacts the first major surface of the base substrate during the transferring.

53. A method according to claim 46, wherein the first major surface of the base substrate comprises a porous surface, and wherein a portion of the anchor polymeric composition infiltrates the porous surface after the transferring.

54. A method according to claim 46, wherein the first major surface of the base substrate comprises fibers, and further wherein the anchor polymeric composition encapsulates at least a portion of at least some of the fibers after the transferring.

55. A method according to claim 46, wherein the first major surface of the base substrate comprises polymeric material with a melt processing temperature at or below a melt processing temperature of the anchor polymeric composition.

56. A method according to claim 46, wherein the elastic component comprises one or more openings formed therethrough.

57. A method according to claim 46, wherein the elastic component comprises a first end and a second end defining a longitudinal axis therebetween, and wherein the elastic component comprises a thickness measured normal to the first major surface of the base substrate, and further wherein the thickness of the elastic component is different at selected locations along the longitudinal axis.

58. A method according to claim 46, wherein the elastic component comprises a first end and a second end defining a longitudinal axis therebetween, and wherein the elastic component comprises a width measured generally transverse to the longitudinal axis and along an in-plane direction on the first major surface of the base substrate, and further wherein the width of the elastic component is different at selected locations along the longitudinal axis.

59. A method according to claim 46, further comprising attaching a cover substrate over the one or more elastic composite structures on the first major surface of the base substrate, wherein the one or more elastic composite structures are located between the base substrate and the cover substrate.

60. A method according to claim 59, wherein the cover substrate is adhesively attached over the one or more elastic composite articles and the first major surface of the base substrate.

61. A method of manufacturing a composite web, the method comprising:

delivering molten elastomeric polymeric composition onto a forming tool;

maintaining the forming tool at a roll temperature that is below a melt processing temperature of the elastomeric polymeric composition;

depositing molten anchor polymeric composition on at least a portion of the elastomeric polymeric composition;

transferring the anchor polymeric composition to a first major surface of a base substrate, wherein the transferring comprises contacting the first major surface of the substrate with the anchor polymeric composition, and wherein the transferred anchor polymeric composition forms anchors attached to the first major surface of the base substrate; and separating the elastomeric polymeric composition from the forming tool after the transferring, wherein the separated elastomeric polymeric composition forms one or more elastic components;

wherein a composite web is formed after the transferring and the separating, with the composite web comprising one or more elastic composite structures on the first major surface of the base substrate, wherein at least one of the elastic composite structures comprises one of the elastic components attached to and extending between at least two of the anchors, and further wherein the elastic component is attached to the first major surface of the substrate between the anchors.

* * * * *